United States Patent [19]

de Schrijver

[11] 4,250,161
[45] Feb. 10, 1981

[54] METHOD AND KIT FOR THE PREPARATION OF RADIOPHARMACEUTICALS

[75] Inventor: Marc de Schrijver, Rosenau, France

[73] Assignee: Solco Basel AG, Basel, Switzerland

[21] Appl. No.: 939,923

[22] Filed: Sep. 6, 1978

[30] Foreign Application Priority Data

Sep. 8, 1977 [CH] Switzerland ............... 11027/77

[51] Int. Cl.³ .................... A61K 43/00; A61K 49/00
[52] U.S. Cl. ........................................ 424/1; 422/61; 424/9
[58] Field of Search ............... 424/1, 9; 422/61, 71

[56] References Cited

U.S. PATENT DOCUMENTS

| | | |
|---|---|---|
| 4,071,613 | 1/1978 | Hunter, Jr. .................. 424/1 |
| 4,087,516 | 5/1978 | Laidler et al. ............... 424/1 |
| 4,104,366 | 8/1978 | Schmidt-Dunker et al. ..... 424/1 |

Primary Examiner—Brooks H. Hunt
Assistant Examiner—Christine M. Nucker
Attorney, Agent, or Firm—Ladas & Parry

[57] ABSTRACT

For labelling organic or anorganic substances with technetium-99m in the heterogenous phase, an aqueous solution of the substance to be labelled is mixed with a pertechnetate and an aqueous suspension of $Sn_2Fe(CN)_6$, $Sn_3[Fe(CN)_6]_2$, SnS or SnTe and the solution of the labelled substance is separated from the solid phase after completion of the reduction of the pertechnetate. In particular, the reducing agent can be in a vial, in lyophilized or adsorbed form, as appropriate together with the substance to be labeled.

11 Claims, No Drawings

METHOD AND KIT FOR THE PREPARATION OF RADIOPHARMACEUTICALS

The radioactive isotope technetium-99m has become increasingly important in nuclear medicine during the last two decades and an end to this development cannot be forseen at present. It is definitely due to its radiological features which are especially suitable for use on humans. The radioisotope is distinguished by a relatively short physical half-life of 6.0 hours and therefore causes only minimum radiation strain for the person being examined or treated. Also of importance in this respect is the kind of radioactive decay which consists in pure gamma radiation, being free from beta radiation. Finally, the energy of the gamma radiation produced (140 KeV) is sufficient to achieve good penetration of the organs and tissues. In addition technetium-99m is easily available.

For these reasons, a number of carriers labelled with technetium-99m are used in medicine today, especially for diagnosis purposes. These preparations allow scintigraphic examination of most body tissues, as especially of the blood, bones, lungs, liver, kidneys and last but not least the identification of various neoplastic tissues (tumours and metastases).

The most common form of compounds of technetium-99m is provided by pertechnetates, especially sodium-99m pertechnetate. Pertechnetate solutions are obtained with the help of the known molybdän-99-generators. In pertechnetates, the technetium-99m is in the 7-valency state, and it must firstly be reduced to a lower valency (mainly Tc(III), Tc(IV) and/or Tc(V)), since only the respective technetium ions can be boned by the carriers—generally by chelation.

The most various methods have been suggested for the reduction of the pertechnetates, among them electrolytic reduction and the use of iron(II)-salts, tin(II)-salts, copper(I)-salts, sodium borohydride, iron(III)-salts in combination with ascorbic acid, thiocyanates, hydrazine etc. Today, the reduction by means of tin(II)-chloride is usually preferred since it can be easily and comfortably carried out in the laboratory. Already, various sets of reagents (kits) are offered, by which the amounts of carrier and tin(II)-chloride calculated for the examination of a patient are combined in an ampoule and give the ready-to-use labelled preparation by adding only the pertechnetate solution.

The use of tin(II)-chloride as reducing agent, however, although easy in application, involves certain drawbacks, some of which are quite serious. Most important thereby is the sensitivity, especially of the solutions, against oxidizing agents in general; the non-stability of the $SnCl_2$-solutions e.g. upon contact with air, necessitates appropriate protection measures. Very often, the excess Sn(II)-ions used will form a chelate with the compound to be labelled.

Further, rather serious disadvantages of reduction by means of water-soluble $SnCl_2$ ($SnCl_2 \cdot 2H_2O$) occur during the practical use of the labelled compound. On the one hand, the tin ions introduced in excess remain in the solution and are introduced into the blood stream together with the labelled compound which is undesirable from a physiological point of view. On the other hand, insoluble tin compounds, e.g. $SnO \cdot H_2O$, are formed by hydrolysis; at the time of labelling, a colloid with technetium-99m is formed from these compounds. This radioactive colloid is administered to the person to be examined with the labelled compound and is taken up by the liver, bone-marrow, spleen etc.. However, this impairs the desired specific accumulation of the radioactivity in a single organ or tissue and therefore makes an unambiguous result of the examination difficult.

A method for labelling organic and inorganic substances, such as diethylene triamine pentaacetic acid (DTPA), sodium-phytate, proteins, 1-hydroxy-ethylidene-1,1-diphosphonic acid (HEDP), acetanilido-imino diacetic acid derivatives, diphosphates, citrates, glucoheptonate etc., with technetium-99m has now been found which is not inferior to the above-mentioned method in practical use as regards simplicity and comfortability, but which does not have its disadvantages and is suitable for all chemical substances which can be labelled with technetium-99m.

The method according to the invention is characterized in that (a) an aqueous solution of the chemical substance to be labelled, (b) the amount of pertechnetate calculated for the labelling and (c) an acqueous suspension of tin(II)-iron cyanide of the formula $Sn_2Fe(CN)_6$ resp. $Sn_3[Fe(CN)_6]_2$ or of tin(II)-sulfide or tin(II)-telluride are mixed together in an amount, which—in respect of the reduction of the pertechnetate ions of the formula $TcO_4^-$ to technetium ions with lower valency—represents an excess, the mixing being carried out in such a way that the pertechnetate (b) or the suspension (c) is added last, the two-phase system obtained is kept in suspension and, after completion of the reduction of the pertechnetate, the solid phase is separated from the solution containing the chemical substance labelled with technetium-99m.

The above-mentioned water-insoluble tin(II)-compounds are used as reducing agents. Up until now, these compounds have only been the subject matter of individual scientific studies; they have not found any technical use and have never been used or even suggested for reducing purposes.

The compounds used in the present invention as reducing agents for the first time, can be produced according to the methods described in the experimental part.

The compounds are stable in a dry state and in closed bottles and this without special measures for the exclusion of oxygen or air. After 6 months' storage it was seen that their reducing capacity had remained unimpaired.

The compounds contemplated by the present invention are practically insoluble, both in cold and warm water. This insolubility allows the reduction to be carried out in a heterogeneous phase; it is therefore not disturbing to put in an excess of reducing agent since the unused portion thereof is removed as an insoluble substance. Series of tests with compounds of various chemical structure (see Examples) have shown that in general an amount of about 0.02–0.25 mg of $Sn_2Fe(CN)_6$, or 0.015–0.18 mg of $Sn_3[Fe(CN)_6]_2$, or 0.12–0.16 mg of SnS, or 0.013–0.17 mg of SnTe per 100 mg carrier is sufficient to achieve the reduction of the amount of pertechnetate used and to achieve a quantitative labelling. This amount of reducing agent corresponds to about 0.06 to 0.70 $\mu M$ (Micromol) Sn(II) in insoluble form per 100 mg of carrier.

For the reduction with $SnCl_2 \cdot 2H_2O$, until now generally 0.5 to 35.0 mg of $SnCl_2 \cdot 2H_2O$ per 100 mg of carrier, i.e. about 0.02 to 15 $\mu M$ of Sn(II)-ions as water-insoluble $SnCl_2 \cdot 2H_2O$ per 1 mg of carrier, was used. In the most favourable case, therefore, one needs about 0.0037 mg of Sn(II)-ions as soluble $SnCl_2 \cdot 2H_2O$ per milligramm of carrier. In comparison, in accordance with the new method, normally at most, as mentioned, 0.0013 mg of Sn(II)-ions (=about 0.007 $\mu M$ of Sn(II)-ions are used as reducing agent in insoluble form per milligramm of carrier. This maximum amount represents about a third of the minimum amount of soluble Sn(II)-ions previously required. If one further considers that the Sn(II)-ions are used according to the new method in the form of an insoluble salt, then practically even less Sn(II)-ions exist in the solution.

In the practical execution of the process, one can use the tin(II)-iron cyanide in an amount of 0.0001 to 0.005 mg, the tin(II)-sulfide and the tin(II)-telluride in an amount of 0.0001 to 0.010 mg - per 1 mg of the chemical substance to be labelled. The above amounts represent a considerable excess of reducing agent; but the range extended upwards covers all possible cases and the excess can be separated from the solution of the labelled substances just as easily as when using an exactly calculated amount (e.g. 0.0025 mg). However, generally, the narrower range of amount mentioned further above, is suitable.

For the use in accordance with the method, it is advantageous to slurry a certain amount of reducing agent in a few ml of distilled water and to convert the slurry by treatment with ultrasonics into a fine, homogeneous suspension.

It should be emphasized that the order of adding the three reaction components (a), (b) and (c) cannot be optionally chosen. The addition must take place in accordance with the definition of the invention since mere mixing of the reducing agent and the pertechnetate, in the absence of the carrier, would destroy the success of the labelling or at least of its quantitative course.

The labelling can take place, for instance, in that during an operation parallel to that of the production of the suspension, a solution of the carrier is produced in as little distilled water as possible with a pH range between 2 and 9 and is treated with the calculated amount of pertechnetate in an aqueous solution. The total volume is advantageously about 0.5 to about 10 ml. The suspension of the reducing agent is then added and the mixture is mixed, shaken or stirred for about 5 to 15 minutes.

After completion of the pertechnetate-reduction and labelling concluded thereby, the unused portion of the reducing agent and the insoluble oxidation product formed can easily be separated from the solution of the labelled chemical substance. The separation of the insoluble substances can take place, among others, by filtering, decanting or centrifuging; but it can also be carried out by adsorption to an inert carrier, e.g. silica gel, or suitable resins (e.g. Sephadex, Biogel; Trademarks).

According to an embodiment of the process according to the invention, the tin(II)-compound and a carrier are mixed together, and the mixture is then lyophilised. The lyophilised mixture can be immediately labelled by the addition of 1 to 6 ml of pertechnetate solution and the solution of the labelled compound can be separated.

Especially advantageous for practical use is an embodiment, in which the labelling reaction is carried out in the vial intended for the subsequent examination and the reducing agent is adsorbed on the ampoule wall which is coated with an appropriate adsorption agent.

The use of tin(II)-telluride as reducing agent offers special advantages. Firstly, it exceeds the other compounds to be used according to the invention as regards insolubility. However, more important in practical use is the possibility of spraying SnTe in a vacuum directly on a glass wall (e.g. of an ampoule) without decomposition and thereby obtaining a paper-thin, well-adsorbed layer of the reducing agent. In this way, the embodiment described above can be very elegantly realized by immediate adsorption on the ampoule-wall, without using a special adsorption agent.

The sterility of the ready-to-use, injectable solution containing the labelled carrier is achieved in accordance with the usual methods, especially in that one starts with a sterile solution and always works under sterile conditions or uses sterile filtration or thermal sterilization at the end of the process. To produce the solutions e.g. water for injection-solutions according to Pharmacopoea Helvetica VI can be used. The sterility of the radioactive solution obtained can be checked, for example according to the test method in U.S. Pharmacopoeia XVIII, the absence of pyrogenic substances in the solution according to the test method in Deutsches Arzneibuch, 7th ed.

The carrier substances labelled according to the method of the invention contain more than 95% of the radioactivity introduced in the form of pertechnetate. This result was confirmed by corresponding measurements carried out on the separated solid substances; they proved to be practically free from radioactivity. The loss of radioactivity caused by the separation of the solids, e.g. by the filtration, is unimportant and can be ignored. It is therefore clear that the radioactivity is not adsorbed in the solid phase nor does it remain joined to it in some other way, but is practically quantitatively bound by the carrier.

The quantitative yield of the labelling reaction is also confirmed by paper chromatography of the solutions obtained since no pertechnetate ion could be found therein; this method can additionally be used to determine the purity of the products of the process. For the chromatography in the ascending method, the solvent consists of a mixture of acetone and methanol 50:50; moreover, Whatman-Paper No. 3 is used. During the development of chromatogramm it is shown that the compounds labelled with technetium-99m have an $R_f$-value of 0.0, while the free pertechnetate ion with an $R_f$-value of about 0.9–1.0 moves towards the front of the solvent. With the chromatography in the descending method, the same solvent system or an ethylene diamine tetracetic acid phosphate buffer and Whatman-Paper No. 1 is used. The chromatogramm is developed for about 3 hours or long enough until the front of the solvent has covered a distance of approximately 20 to 25 cm; it is then dried in the air and tested for radioactivity. The labelled compounds have in the mentioned buffer system an $R_f$-value of 0.9 to 1.0 and the pertechnetate an $R_f$-value of 0.5 to 0.6.

A further confirmation of the quantitative yield during the labelling is given lastly by the biological check. A solution of sodium phytate labelled in accordance with the invention was administered to 6 adult rabbits in the ear vein. It is known that free pertechnetate ion behaves in the organism very similarly to iodione ion in respect of transport, distribution and accumulation: it is mainly taken up by the thyroid gland. About 20 to 30 minutes after administration, the test animals were examined by means of a gamma camera for the distribution of radioactivity. It was shown thereby that the thyroid gland did not give any measurable radioactivity in any of the animals; the radioactivity was found mainly in the liver with a small part in the spleen and in the bone marrow. These results show that the radioactivity is not due to the pertechnetate remaining in the solution, but only to the labelled carrier compound.

The results therefore correspond with the findings in the labelling of phytate according to the known method.

The compounds labelled according to the invention show a remarkable stability within the useful period of time caused by the half-life of the technetium-99m (6.0 hours). Thus it has been observed that 8 hours after the labelling, less than 5% of the radioactivity is in the form of free technetium ions.

In order to obtain information about the fate of the tin ions becoming free during the reduction of the pertechnetate, the respective $^{113}Sn_2[Fe(CN)_6]$ was produced according to the method described for $Sn_2[Fe(CN)_6]$, but using $^{113}SnCl_2$ and normal $SnCl_2$ as carrier. Using this radioactive reducing agent, the same carriers were labelled as described in the following Examples. It was shown when testing the labelled compounds that tin(II)-ions are bonded thereto. The amount of bonded tin ions depends on the chemical structure of the carrier. It also appears to be influenced by the pH-value of the solution.

Totally, the following advantages are given from the labelling according to the invention of organic and inorganic substances with Technetium-99m in the heterogeneous phase:

1. Due to the insolubility of the reducing agent used, its excess can be easily and completely separated from the solution of the labelled compound. In this way, the draw-backs of the previous reduction with tin(II)-chloride mentioned at the beginning (necessity of protective measures against oxidation, introduction of the excess of tin ions into the blood stream, formation of a radioactive Sn-$^{99m}$Tc-colloid and impairment of a specific accumulation caused therefrom) are overcome.

2. With the labelling method according to the invention, at the most 0.0025 mg of a reducing agent are generally used per 100 mg of carrier, which corresponds to 0.70 $\mu$m tin(II)-ions in water-insoluble form. This is not only considerably less than the minimum amount of soluble tin(II)-ions used until now, but it also becomes possible to control the amount of tin-ions bonded by the labelled compound within certain limits.

3. The calculated amount of reducing agent can be stored in ampoules in sterile and pyrogene-free conditions. The contents of such ampoules (kits) can be mixed with the desired carrier according to necessity shortly before use and labelled with $^{99m}$-pertechnetate. This allows more flexibility of use.

4. The ready-to-use kits which contain the lyophilized carrier and the pulverized reducing agent or the reducing agent adsorbed on the ampoule wall, are distinguished by total stability. The storage in a solid, dry state with the exclusion of oxygen or air, hinders both a subsequent oxidation and the formation and precipitation of insoluble, basic tin-compounds.

It must be understood that the advantages mentioned are not gained by an impairment in the labelling because its yield in regard to the amount of radioactivity of the pertechnetate used is over 95%.

Only pyrogene-free substances resp. pyrogene-free and sterile solutions may be used in the process. All steps must be carried out under aseptic and pyrogene-free conditions.

The following Examples should describe the invention in more detail.

EXPERIMENTAL PART

A. Preparation of $Sn_2Fe(CN)_6$

Solution 1: 5.5 g of $SnCl_2 \cdot 2H_2O$ are dissolved in 55 ml 2-N HCl. The solution is sterile filtered over a 0.2 $\mu$-Millex-filter manufactured by Millipore.

Solution 2: 10.0 g of $K_4Fe(DN)_6 \cdot 3H_2O$ are dissolved in 80 ml of distilled water and the solution is subsequently sterile filtered over a 0.2 $\mu$-Millex-filter of Millipore.

(a) In a nitrogen atmosphere, 70 ml of freshly prepared solution 2 are slowly added dropwise at about $+22°$ C. under thorough stirring to 50 ml of freshly prepared solution 1, whereby a white, voluminous, gel-like precipitate is formed. For complete precipitation, the reaction mixture is stirred for about further 15 minutes. After centrifugation (about 2500 rpm for 15 Mins.) the precipitate is isolated. The precipitate is suspended in about 50 ml of 1N HCl, then centrifuged. To completely remove any possible remaining tin(II)-ions or $[Fe(CN)_6]^{4-}$ -ions, the washing procedure is repeated with $3 \times 50$ ml of 1N HCl. The product is slurried in about 60 ml of distilled water, then certrifuged. To completely remove HCl, this procedure is repeated with $5 \times 60$ ml of distilled water. The precipitate is washed with $3 \times 60$ ml of anhydrous ethanol and subsequently dried in a vacuo.

(b) 50 ml of freshly prepared solution 1 are heated in a nitrogen atmosphere to about 70° C. Then 70 ml of freshly prepared solution 2 are slowly added dropwise while being vigorously stirred until no blue coloring results. After about another half-hour of stirring at this temperature, the reaction mixture is cooled off to $+22°$ C. The precipitate is separated by filtration, slurried in about 50 ml of 1N HCl and then filtered off again. The purifying and drying process takes place as in part (a).

B. Preparation of $Sn_3[Fe(CN)_6]_2$ 50 ml of freshly prepared solution 1 of section A are treated in a nitrogen atmosphere at about $+5°$ C., while being vigorously stirred, with 50 ml of 1N freshly prepared $K_3Fe(CN)_6$-solution. The addition of the $K_3Fe(CN)_6$-solution is carried out very slowly (about 15 minutes per drop), so that $Sn_3[Fe(CN)_6]_2$ precipitates immediately. After the reaction has ended, the white precipitate is immediately isolated by centrifugation. To completely remove any remaining foreign ions, the precipitate is washed with $3 \times 60$ ml of 0.01-N HCl at about $+5°$ C. The further purification with distilled water and anhydrous ethanol and the drying, are carried out as in paragraph A, part (a).

C. Preparation of tin(II)-sulfide (a) 50 ml of freshly prepared solution 1 from Section A are adjusted with 2-N acetate buffer to a value of 5.0. Then 50 ml of 2N ammonium sulfide are added dropwise. The precipitate is filtered off and washed with distilled water and anhydrous ethanol.

(b) 50 ml of freshly prepared Solution 1 from Section A are adjusted with 2N acetate buffer to a pH-value of 5.0. Then an excess of hydrogen sulfide gas is introduced. The resulting precipitate is filtered off, washed with distilled water and anhydrous ethanol and then dried in a vacuo.

D. Preparation of tin(II)-telluride

Tin(II)-telluride is available on the market (e.g. from Ventron GmbH, Karlsruhe (FRG), under order no. 89

186). It can also be prepared from a Sn(II)-salt solution and H$_2$Te-gas, as follows.

The H$_2$Te-gas is produced from Al$_2$Te$_3$ and 4N hydrochloric acid in a Kipp's apparatus, under the exclusion of oxygen, whereby 4N hydrochloric acid is previously boiled and then cooled to room temperature in a nitrogen atmosphere.

10.0 g of SnCl$_2$·2H$_2$O are dissolved in 200 ml of water. The precipitate formed by partial hydrolysis is dissolved again by adding 6N ammonium hydroxide solution. After microfiltration over an 0.2 $\mu$ Millex-filter, the solution is put into a 750 ml reaction vessel under the exclusion of oxygen, this reaction vessel being provided with a gas-introducing tube, a stirrer and a gas-collecting vessel containing 2N sodium hydroxide solution.

H$_2$Te-gas is introduced into the tin(II)-solution while being stirred; SnTe precipitates as black flakes. After completion of the reaction, the precipitate is filtered off and washed with water. The precipitate is then suspended in 300 ml of water and the suspension is heated to the boiling point under exclusion of oxygen for 3 hours and subsequently left to stand for 24 hours at room temperature. The precipitate is filtered off, washed with anhydrous ethanol and dried in vacuo.

EXAMPLE 1

(a) Under aseptic conditions, 25.0 mg Sn$_2$Fe(CN)$_6$ are finely homogenized in a 100 ml-measuring flask firstly in about 50 ml sterile, pyrogene-free water in a nitrogen atmosphere with the help of an ultrasonic bath from Brausonic. The homogenisate is diluted with water to a volume of 100 ml and then kept in an autoclave for 2 hours at 80° C. 1 ml corresponds to 250 $\mu$g Sn$_2$Fe(CN)$_6$.

(b) By means of a suitable automatic pump, each 0.2 ml (or 0.1 ml) of the homogenisate of Example 1a is divided into 10 ml vials and lyophilised; subsequently, the vials with the lyophilisate are sealed in a nitrogen atmosphere.

0.2 ml homogenisate contains 50 $\mu$g Sn$_2$Fe(CN)$_6$—lyophilisate 0.1 ml homogenisate contains 25 $\mu$g Sn$_2$Fe(CN)$_6$—lyophilisate (c) 4.0 g N-(2,6-diethyl acetanilido)—imino diacetic acid are suspended in about 70 ml distilled water. For dissolving, the substance is converted into its sodium salt by adding 2 N NaOH. The clear solution has a pH-value of about 9.0. After dissolution, the pH-value is adjusted to 6.5 by adding 1N HCl. The solution is diluted with distilled water to 100 ml and sterile filtered over an 0.2 $\mu$-Millex-filter. Each 1.0 ml of the solution is divided into 10 ml-ampoules and subsequently lyophilised. The vials with the lyophilisate are sealed in a nitrogen atmosphere. 1 vial contains 40 mg of the active substance, i.e. N-(2,6-diethyl acetanilido) imino diacetic acid.

Labelling: Each 2 to 6 ml (containing 1 to 40 mCi) $^{99m}$Tc—pertechnetate are injected into the vial containing the active substance. After complete dissolution, 50 $\mu$g Sn$_2$Fe(CN)$_6$—lyophilisate (Example 1b) are injected into the solution in the vial. The suspension is homogenized by light shaking. After 5 to 10 minutes, the suspension is filtered off over an 0.2 $\mu$-Millex-filter from Millipore. The filtrate is used.

EXAMPLE 2

4,0 g of N—(2.6-diethylacetanilido)—iminodiacetic acid are dissolved (PH~9.0) in about 50 ml distilled water by adding 5-N NaOH. By adding 2N HCl, the pH is adjusted to 6.5. The clear solution is sterile filtered through an 0.2 $\mu$-Millipore-filter and rinsed with about 10 ml of distilled water. After adding 20 ml of Sn$_2$Fe(CN)$_6$—homogenisate from Example 1a, the suspension is diluted with distilled water to a final volume of 100 ml. The suspension is divided, while being continuously stirred, into a volume of each 1.0 ml into 10 ml-vials and is then lyophilised. The vials with the lyophilisate are sealed in a nitrogen atmosphere. 1 vial contains 40,0 mg of active substance, namely N-(2,6-diethylacetanilido)-iminodiacetic acid and 50 $\mu$g Sn$_2$Fe(CN)$_6$.

Labelling: Each 2 to 6 ml (containing 1 to 40 mCi) $^{99m}$Tc—pertechnetate is injected into the vials containing the active substance and the reducing agent. It is homogenized by shaking, and after 5 to 10 minutes, the suspension is filtered off over an 0.2 $\mu$-Millex-filter. The filtrate is used.

EXAMPLE 3

2.0 g of the anhydrous sodium salt of inosithexaphosphoric acid (sodium phytate) are dissolved in about 50 ml of distilled water (pH~10). By adding 2N HCl, the pH is adjusted to 6.5. The clear solution is sterile filtered through an 0.2 $\mu$-Millipore-filter and rinsed with about 10 ml of distilled water. After adding 20 ml of Sn$_2$Fe(CN)$_6$-homogenisate from Example 1a, the suspension is diluted with distilled water to a final volume of 100 ml. The suspension is divided, while stirring continuously, to a volume of each 1.0 ml into 10 ml-vials and is then lyophilised. The vials with the lyophilisate are sealed in a nitrogen atmosphere. 1 ampoule contains 20 mg of the active substance, i.e. sodium phytate and 50 $\mu$g Sn$_2$Fe(CN)$_6$.

The labelling is carried out in accordance with Example 2.

EXAMPLE 4

2.5 g of tetrasodiumdiphosphate decahydrate and 150 mg of ascorbic acid are dissolved in about 50 ml of distilled water (pH~7 to 8). By adding 0.5N HCl, the pH is adjusted to 6.0. The clear solution is sterile filtered over an 0.2 $\mu$-Millipore-filter and subsequently rinsed with about 10 ml of distilled water. 15 ml Sn$_2$Fe(CN)$_6$—homogenisate from Example 1a are added to the filtrate while stirring, and the suspension is diluted with distilled water to a final volume of 100 ml. To lyophilize each 1.0 ml is filled into 10 ml-vials, and the vials with the lyophilisate are sealed in a nitrogen atmosphere. 1 vial contains 15 mg tetrasodium diphospate, 1.5 mg of ascorbic acid and 37.5 $\mu$g of Sn$_2$Fe(CN)$_6$. The labelling is carried out as in Example 2.

EXAMPLE 5

2.4 g of diethylenetriamine pentaacetic acid (DTPA) are suspended in about 50 ml of distilled water. For dissolving, the pH is increased to 9 to 10 by adding 5N NaOH, then adjusted to 7.0 by adding 1N HCl. The clear solution is sterile filtered over an 0.2 $\mu$-Millipore-filter and then rinsed with about 10 ml of distilled water. 2.0 ml of Sn$_2$Fe(CN)$_6$ homogenisate of Example 1a are added to this filtrate, while stirring, and the suspension is diluted with distilled water to a final volume of 100 ml. To lyophilise, each 1.0 ml is filled into 10 ml-ampoules, and the ampoules with the lyophilisate are sealed in a nitrogen atmosphere. 1 ampoule contains 24 mg of DTPA and 5 $\mu$g of Sn$_2$Fe(CN)$_6$.

The labelling takes place as in Example 2.

EXAMPLE 6

20 g of 1-hydroxy ethylidene-1,1-diphosphonic acid (HEDP) are dissolved in about 50 ml of distilled water (pH ~1.5). By adding 5N NaOh, the pH is adjusted to 6.5.The clear solution is sterile filtered over an 2.0 $\mu$-Millipore-filter and then rinsed with about 10 ml of distilled water. 2.0 ml of $Sn_2Fe(CN)_6$ homogenisate from Example 1a are added dropwise while being stirred.

After adjusting the final volume to 100 ml with distilled water, each 1.0 ml of the suspension is lyophilized in 10 ml-ampoules. The ampoules with the lyophilisate are sealed in a nitrogen atmosphere. 1 ampoule contains 20 mg of HEDP and 5 $\mu$g of $Sn_2Fe(CN)_6$.

The labelling takes place as in Example 2.

EXAMPLE 7

20.0 g of calcium glucoheptonate are dissolved by adding 10 ml of O. 1N HCl in about 120 ml distilled water; after 5 minutes, the pH-value is adjusted to 6.0 with 0.1N NaOH. The clear solution is sterile filtered over an 0.2-Millipore-filter and then rinsed with about 10 ml of distilled water. 16.0 ml $Sn_2Fe(CN)_6$ homogenisate from Example 1a are added dropwise while stirring, and then the suspension is diluted with distilled water to 200 ml. To lyophilize, each 2.0 ml of the suspension are put in 10 ml-ampoules. The ampoules with the lyophilisate are sealed in a nitrogen atmosphere. 1 ampoule contains 200 mg of calcium glucoheptonate and 40 $\mu$g of $Sn_2Fe(CN)_6$.

The labelling takes place as in Example 2.

E. Preparation of radioactive $^{113}Sn_2Fe(CN)_6$

Solution 1: 200 mg of $SnCl_2 \cdot 2H_2O$ are dissolved in 2.0 ml of 2N HCl. The solution is filtered through an 0.2 $\mu$-Millex-filter of Millipore.

1 ml contains 100 mg of $SnCl_2.2H_2O$.

Solution 2: 240 mg of $K_4Fe(CN)_6 \cdot 3H_2O$ are dissolved in 2.0 ml of 2N HCl and the solution is subsequently filtered over an 0.2 $\mu$-Millex-filter of Millipore.

1 ml contains 120 mg of $K_4Fe(CN)_6 \cdot 3H_2O$.

Solution 3: 20 mCi (=2 mg) of sodium-$^{113}$Sn-hexachlorostanate (Amersham/England) in 6-molar HCl are neutralized with 5N NaOH to pH~4. After adjusting the pH to 5.5 with 2 N sodium acetate, the $^{113}$Sn(IV)-solution is reduced with 2 N ammonium sulfide to $^{113}$Sn(II). The precipitate of $^{113}$Sn—sulfide is isolated by centrifuging and washed with 0.2-molar acetate buffer (pH=6.5). The precipitate is dissolved in 2 ml of 6N HCl and heated for about 5 minutes to boiling in order to remove the hydrogen sulfide. Subsequently, the insoluble portion is removed by centrifuging. The filtrate (~2 ml) contains $^{113}SnCl_2$. The specific activity is about 10 mCi/ml.

Preparation: 0.5 ml of the freshly prepared solution 1 and 0.2 ml of the freshly prepared solution 3 (containing 2 mCi) are mixed in a nitrogen atmosphere. While stirring, 0.8 ml of the solution 2 are added dropwise. For complete reaction, the suspension is stirred for a further period of about 30 minutes. The precipitate is isolated by centrifuging. To completely remove any possible remaining foreign ions, the precipitate is washed with 4×3 ml of 1N HCl, 4×5 ml of distilled water and 3×5 ml of anhydrous ethanol. The precipitate is dried in vacuo (15 mm Hg) to about +35° C. The yield is about 100 mg. The specific activity is 1 mCi in 5 mg of $^{113}Sn_2Fe(CN)_6$.

For further examinations, the radioactive $^{113}Sn_2Fe(CN)_6$ precipitate is treated as in Example 1a.

EXAMPLE 8

The preparation of sodium phytate kits takes place in accordance with Example 3 and with the radioactive $^{113}Sn_2Fe(CN)_6$ resulting from Section E. After labelling the product with $^{99m}$pertechnetate, the activity distribution of $^{113}$Sn is checked. 80 to 90% of the $^{113}$Sn-activity was found in bonded form ($^{99m}$Tc phytate).

EXAMPLE 9

The preparation of N-(2,6-diethylacetanilido)-imino diacetic acid kits takes place according to Example 2 with $^{113}Sn_2Fe(CN)_6$ from Section E. After labelling with $Na^{99m}TcO_4$-solution, 65 to 75% of the $^{113}$Sn-activity was found in bonded form ($^{99m}$Tc-[N-(2,6-diethyl acetanilido)-iminodiacetic acid].

EXAMPLE 10

The preparation of calcium glucoheptonate kits takes place according to Example 7 with $^{113}SN_2Fe(CN)_6$ from Section E. After labelling with $Na$-$^{99m}$Tc-pertechnetate, 8 to 12% of the $^{113}$Sn-activity was found in bonded form ($^{99m}$Tc-glucoheptonate).

EXAMPLE 11

(a) Under aseptic conditions, 350 mg of powdered $Sn_3[Fe(CN)_6]_2$ are firstly finely homogenized in a 100 ml-measuring flask in about 20 ml of sterile, pyrogene-free water in a nitrogen atmosphere with the help of an ultrasonic bath from Brausonic. The homogenisate is diluted with water to a volume of 100 ml and then sterilized for 2 hours in an autoclave at 80° C. 1 ml corresponds to 3.5 mg of $Sn_3[Fe(CN)_6]_2$.

(b) As in Example 3, 2.0 g of anhydrous sodium phytate are dissolved, sterilized and filtered. Then 1 ml of $Sn_1[Fe(CN)_6]_2$ homogenisate from Section (a) is added and the mixture is diluted to a final volume of 100 ml. The suspension is divided in a volume of each 1.0 ml into 10 ml-ampoules, while being continuously stirred, and then lyophilized. 1 ampoule contains 20 mg of Na-phytate and 35 $\mu$g of $Sn_3[Fe(CN)_6]_2$. The labelling takes place as in Example 2.

EXAMPLE 12

As in Example 5, diethylene triaminepentaacetic acid (DTPA) is treated with 0.1 ml of $Sn_3[Fe(CN)_6]_2$ homogenisate from Example 11a. After lyophilization, 1 ampoule contains 24 mg of DTPA and 3.5 $\mu$g of $Sn_3[Fe(CN)_6]_2$. The labelling takes place as in Example 2.

EXAMPLE 13

As in Example 11a, an SnS-homogenisate having a concentration of 3.0 mg of SnS per 1 ml homogenisate is prepared. From this, the ready-to-use kits of Na-phytate resp. DTPA are prepared as in Examples 3 resp. 5. 1 ampoule of the Naphytate kit contains 20 mg of active substance of 30 $\mu$g of SnS. 1 ampoule of the DTPA-kit contains 24 mg of active substance and 3 $\mu$g of SnS.

EXAMPLE 14

As in the previous Examples, the ready-to-use kits of Na-phytate resp. DTPA in a concentration of 20 mg of Na-phytate and 30 $\mu$g of SnTe resp. of 24 mg of DTPA and 3 $\mu$g of SnTe are prepared.

What is claimed is:

1. A method of preparing radiopharmaceuticals with the isotope-99m, comprising mixing (a) an aqueous solution of the chemical substance to be labelled, (b) the amount of pertechnetate calculated for the labelling and (c) an aqueous suspension of a reducing agent selected from the group consisting of $Sn_2Fe(CN)_6$, $Sn_3[Fe(CN)_6]_2$, tin(II)-sulfide and tin(II)-telluride, in an amount which in respect of the reduction of the pertechnetate ions of the formula $TcO-$ to technetium ions with lower valency represents an excess, wherein (a), (b) and (c) are mixed together in such a way that either the pertechnetate (b) or the suspension (c) is added last; keeping the two-phase system obtained in suspension until after completion of the reduction of the pertechnetate, the separating the solid phase from the solution containing the chemical substance labelled with technetium-99m.

2. The method according to claim 1, which comprises using said $Sn_2Fe(CN)_6$ or said $Sn_3[(CN)_6]_2$ in an amount of 0.0001 to 0.005 mg per milligram of the chemical substance to be labelled.

3. The method according to claim 1, which comprises using said tin(II)-telluride or said tin(II)-sulfide in an amount of 0.0001 to 0.010 mg per milligram of the chemical substance to be labelled.

4. The method of any one of claims 1, 2 or 3, wherein the pH-value of the solution (a) is 2 to 9.

5. The method of any one of claims 1, 2 or 3, wherein the separation of the solid phase is carried out by filtration, decantation, centrifugation or adsorption on a suitable surface.

6. The method according to any one of claims 1, 2 or 3, wherein the solution (a) and the suspension (c) are mixed, the mixture is lyophilized and the lyophilisate is treated with the solution (b).

7. An ampoule to carry out the method according to claim 5, wherein the wall of said ampoule is coated with a suitable inert adsorption agent and that said reduction agent is adsorbed on the adsorption agent.

8. An ampoule to carry out the method according to claim 6, comprising the lyophilisate of a mixture of the solution (a) and the suspension (c).

9. An ampoule to carry out the method according to claim 5, wherein the wall of said ampoule is coated with a layer of adsorbed tin(II)-telluride.

10. The ampoule according to claim 7, which contains a solution of the chemical substance to be labelled.

11. The ampoule according to claim 9, which contains a solution of the chemical substance to be labelled.